(12) United States Patent
Black et al.

(10) Patent No.: US 9,453,526 B2
(45) Date of Patent: Sep. 27, 2016

(54) BOTTOM-LOADING ANCHOR ASSEMBLY

(71) Applicant: DeGen Medical, Inc., Florence, SC (US)

(72) Inventors: Craig Black, Florence, SC (US);
Rakesh P. Chokshi, Florence, SC (US);
Willie S. Edwards, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 334 days.

(21) Appl. No.: 13/873,572

(22) Filed: Apr. 30, 2013

(65) Prior Publication Data

US 2014/0321945 A1    Oct. 30, 2014

(51) Int. Cl.
*A61B 17/70* (2006.01)
*F16B 29/00* (2006.01)

(52) U.S. Cl.
CPC ........... *F16B 29/00* (2013.01); *A61B 17/7037* (2013.01)

(58) Field of Classification Search
CPC .......... A61B 17/7001; A61B 17/7002; A61B 17/7032; A61B 17/7034; A61B 17/7035; A61B 17/7037
USPC ................................. 606/246–278, 300–321
See application file for complete search history.

(56) References Cited

U.S. PATENT DOCUMENTS

| | | |
|---|---|---|
| 3,433,510 A | 3/1969 | Hulterstrum |
| 4,273,116 A | 6/1981 | Chiquet |
| 4,419,026 A | 12/1983 | Leto |
| 4,483,334 A | 11/1984 | Murray |
| 4,570,982 A | 2/1986 | Blose et al. |
| 4,693,240 A | 9/1987 | Evans |
| 4,708,510 A | 11/1987 | McConnell et al. |
| 4,763,644 A | 8/1988 | Webb |
| 4,805,602 A | 2/1989 | Puno et al. |
| 4,836,196 A | 6/1989 | Park et al. |
| 4,841,959 A | 6/1989 | Ransford |

(Continued)

FOREIGN PATENT DOCUMENTS

| | | |
|---|---|---|
| DE | 19509332 | 8/1996 |
| DE | 19507141 | 12/2004 |

(Continued)

OTHER PUBLICATIONS

European Patent Office, International Search Report and Written Opinion, Patent App. No. PCT/US2014/036028, Aug. 5, 2014, pp. 1-10.

(Continued)

*Primary Examiner* — Ellen C Hammond
*Assistant Examiner* — Christina Negrellirodrigue
(74) *Attorney, Agent, or Firm* — Buchanan Nipper

(57) ABSTRACT

Anchor assemblies useful for connecting structures to each other are described. An anchor assembly includes a head member and an anchor. In the fully assembled anchor assembly, the anchor is partially disposed within the head member. During assembly, the proximal end of the anchor can be inserted into an opening defined by a distal end of the head member. A retaining member maintains a portion of the anchor within a portion of the head member after assembly. In an embodiment, a compression member enables movement of the retaining member within the head member to allow insertion of a portion of the anchor and subsequent maintenance of the portion of the anchor within a portion of the head member.

3 Claims, 10 Drawing Sheets

(56) References Cited

U.S. PATENT DOCUMENTS

| | | |
|---|---|---|
| 4,854,304 A | 8/1989 | Zielke |
| 4,867,144 A | 9/1989 | Karas et al. |
| 4,887,595 A | 12/1989 | Heinig et al. |
| 4,887,596 A | 12/1989 | Sherman |
| 4,946,458 A | 8/1990 | Harms et al. |
| 5,002,542 A | 3/1991 | Frigg |
| 5,005,562 A | 4/1991 | Cotrel |
| 5,084,049 A | 1/1992 | Asher et al. |
| 5,085,660 A | 2/1992 | Lin |
| 5,092,893 A | 3/1992 | Smith |
| 5,129,388 A | 7/1992 | Vignaud et al. |
| 5,129,900 A | 7/1992 | Asher et al. |
| 5,133,716 A | 7/1992 | Plaza |
| 5,133,717 A | 7/1992 | Chopin |
| 5,176,678 A | 1/1993 | Tsou |
| 5,207,678 A | 5/1993 | Harms et al. |
| 5,217,497 A | 6/1993 | Mehdian |
| 5,257,993 A | 11/1993 | Asher et al. |
| 5,261,909 A | 11/1993 | Sutterlin et al. |
| 5,261,912 A | 11/1993 | Frigg |
| 5,312,404 A | 5/1994 | Asher et al. |
| 5,312,405 A | 5/1994 | Korotko et al. |
| 5,330,477 A | 7/1994 | Crook |
| 5,360,431 A | 11/1994 | Puno et al. |
| 5,364,399 A | 11/1994 | Lowery et al. |
| 5,395,371 A | 3/1995 | Miller et al. |
| 5,429,639 A | 7/1995 | Judet |
| 5,437,671 A | 8/1995 | Lozier et al. |
| 5,443,467 A | 8/1995 | Biedermann et al. |
| 5,466,237 A | 11/1995 | Byrd et al. |
| 5,470,333 A | 11/1995 | Ray |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,496,321 A | 3/1996 | Puno et al. |
| 5,498,262 A | 3/1996 | Bryan |
| 5,498,263 A | 3/1996 | DiNello et al. |
| 5,501,684 A | 3/1996 | Schlapfer et al. |
| 5,520,690 A | 5/1996 | Errico et al. |
| 5,527,314 A | 6/1996 | Brumfield et al. |
| 5,531,746 A | 7/1996 | Errico et al. |
| 5,545,164 A | 8/1996 | Howland |
| 5,549,608 A | 8/1996 | Errico et al. |
| 5,554,157 A | 9/1996 | Errico et al. |
| 5,562,661 A | 10/1996 | Yoshimi et al. |
| 5,569,247 A | 10/1996 | Morrison |
| 5,575,792 A | 11/1996 | Errico et al. |
| 5,578,033 A | 11/1996 | Errico et al. |
| 5,584,834 A | 12/1996 | Errico et al. |
| 5,586,984 A | 12/1996 | Errico et al. |
| 5,591,165 A | 1/1997 | Jackson |
| 5,591,166 A | 1/1997 | Bernhardt et al. |
| 5,601,552 A | 2/1997 | Cotrel |
| 5,601,553 A | 2/1997 | Trebing et al. |
| 5,607,426 A | 3/1997 | Ralph et al. |
| 5,609,593 A | 3/1997 | Errico et al. |
| 5,609,594 A | 3/1997 | Errico et al. |
| 5,628,740 A | 5/1997 | Mullane |
| 5,643,261 A | 7/1997 | Schafer et al. |
| 5,643,265 A | 7/1997 | Errico et al. |
| 5,647,873 A | 7/1997 | Errico et al. |
| 5,669,910 A | 9/1997 | Korhonen et al. |
| 5,669,911 A | 9/1997 | Errico et al. |
| 5,672,176 A | 9/1997 | Biedermann et al. |
| 5,681,319 A | 10/1997 | Biedermann et al. |
| 5,688,272 A | 11/1997 | Montague et al. |
| 5,688,273 A | 11/1997 | Errico et al. |
| 5,690,630 A | 11/1997 | Errico et al. |
| 5,716,355 A | 2/1998 | Jackson et al. |
| 5,716,357 A | 2/1998 | Rogozinski |
| 5,725,528 A | 3/1998 | Errico et al. |
| 5,725,588 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,810,818 A | 9/1998 | Errico et al. |
| 5,817,094 A | 10/1998 | Errico et al. |
| 5,863,293 A | 1/1999 | Richelsoph |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,947,966 A | 9/1999 | Drewry et al. |
| 5,954,725 A | 9/1999 | Sherman et al. |
| 5,961,517 A | 10/1999 | Biedermann et al. |
| 5,964,760 A | 10/1999 | Richelsoph |
| 5,980,523 A | 11/1999 | Jackson |
| 6,010,503 A | 1/2000 | Richelsoph et al. |
| 6,015,409 A | 1/2000 | Jackson |
| 6,019,759 A | 2/2000 | Rogozinski |
| 6,022,350 A | 2/2000 | Ganem |
| 6,050,997 A | 4/2000 | Mullane |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,080,156 A | 6/2000 | Asher et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,600 A | 9/2000 | Drummon et al. |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,183,472 B1 | 2/2001 | Lutz |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,261,287 B1 | 7/2001 | Metz-Stavenhagen |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,302,888 B1 | 10/2001 | Mellinger et al. |
| 6,309,391 B1 | 10/2001 | Crandall et al. |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,382,436 B1 | 5/2002 | Wang |
| 6,383,190 B1 | 5/2002 | Preissman |
| 6,402,752 B2 | 6/2002 | Schaffler-Wachter et al. |
| 6,436,100 B1 | 8/2002 | Berger |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,537,276 B2 | 3/2003 | Metz-Stavenhagen |
| 6,540,748 B2 | 4/2003 | Lombardo |
| 6,547,790 B2 | 4/2003 | Harkey, III et al. |
| 6,551,320 B2 | 4/2003 | Lieberman |
| 6,554,832 B2 | 4/2003 | Shluzas |

(56) References Cited

U.S. PATENT DOCUMENTS

| | | |
|---|---|---|
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,641,586 B2 | 11/2003 | Varieur |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,672,788 B2 | 1/2004 | Hathaway |
| 6,673,073 B1 | 1/2004 | Schafer |
| 6,676,661 B1 | 1/2004 | Martin-Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,830 B2 | 6/2004 | Minfelde et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,905,500 B2 | 6/2005 | Jeon et al. |
| 6,932,817 B2 | 8/2005 | Baynham et al. |
| 6,945,972 B2 | 9/2005 | Frigg et al. |
| 6,951,561 B2 | 10/2005 | Warren et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Fried et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,008,422 B2 | 3/2006 | Foley et al. |
| 7,018,378 B2 | 3/2006 | Biedermann et al. |
| 7,018,379 B2 | 3/2006 | Drewry et al. |
| RE39,089 E | 5/2006 | Ralph et al. |
| 7,066,397 B2 | 6/2006 | Astachow et al. |
| 7,066,937 B2 | 6/2006 | Shluzas |
| 7,087,057 B2 | 8/2006 | Konieczynski et al. |
| 7,128,743 B2 | 10/2006 | Metz-Stavenhagen |
| 7,144,396 B2 | 12/2006 | Shluzas |
| 7,163,538 B2 | 1/2007 | Altarac et al. |
| 7,223,268 B2 | 5/2007 | Biedermann |
| 7,306,606 B2 | 12/2007 | Sasing |
| 7,322,981 B2 | 1/2008 | Jackson |
| 7,335,202 B2 | 2/2008 | Matthis et al. |
| 7,445,627 B2 | 11/2008 | Hawkes et al. |
| 7,476,239 B2 | 1/2009 | Jackson |
| 7,497,869 B2 | 3/2009 | Justis |
| 7,572,279 B2 | 8/2009 | Jackson |
| 7,604,656 B2 | 10/2009 | Shluzas |
| 7,625,396 B2 | 12/2009 | Jackson |
| 7,682,377 B2 | 3/2010 | Konieczynski et al. |
| 7,717,944 B2 | 5/2010 | Foley et al. |
| 7,727,261 B2 | 6/2010 | Barker et al. |
| 7,749,232 B2 | 7/2010 | Salerni |
| 7,749,258 B2 | 7/2010 | Biedermann et al. |
| 7,763,055 B2 | 7/2010 | Foley |
| 7,857,834 B2 | 12/2010 | Boschert |
| 7,862,595 B2 | 1/2011 | Foley et al. |
| 7,867,259 B2 | 1/2011 | Foley et al. |
| 7,875,065 B2 | 1/2011 | Jackson |
| 7,887,539 B2 | 2/2011 | Dunbar, Jr. et al. |
| 7,892,238 B2 | 2/2011 | DiPoto et al. |
| 7,918,878 B2 | 4/2011 | Songer et al. |
| 7,922,727 B2 | 4/2011 | Songer et al. |
| 7,942,909 B2 | 5/2011 | Hammill, Sr. et al. |
| 7,942,910 B2 | 5/2011 | Doubler et al. |
| 7,942,911 B2 | 5/2011 | Doubler et al. |
| 7,947,065 B2 | 5/2011 | Hammill, Sr. et al. |
| 7,951,173 B2 | 5/2011 | Hammill, Sr. et al. |
| 8,002,806 B2 | 8/2011 | Justis |
| 8,038,699 B2 | 10/2011 | Cohen et al. |
| 8,075,603 B2 | 12/2011 | Hammill, Sr. et al. |
| 8,092,460 B2 | 1/2012 | Geist et al. |
| 8,105,362 B2 | 1/2012 | Duarte |
| 8,123,751 B2 | 2/2012 | Shluzas |
| 8,133,262 B2 * | 3/2012 | Whipple ............ A61B 17/7037 606/265 |
| 8,147,522 B2 | 4/2012 | Warnick |
| 8,192,439 B2 | 6/2012 | Songer et al. |
| 8,197,518 B2 | 6/2012 | Hammill, Sr. et al. |
| 8,236,035 B1 | 8/2012 | Bedor |
| 8,246,624 B2 | 8/2012 | Forton et al. |
| 8,267,978 B2 * | 9/2012 | Lindemann ......... A61B 17/685 606/267 |
| 8,361,124 B2 | 1/2013 | Sherman et al. |
| 2002/0103487 A1 | 8/2002 | Errico et al. |
| 2002/0161368 A1 | 10/2002 | Foley et al. |
| 2003/0004512 A1 | 1/2003 | Farris et al. |
| 2003/0045879 A1 | 3/2003 | Minfelde et al. |
| 2003/0060826 A1 | 3/2003 | Foley et al. |
| 2003/0100896 A1 | 5/2003 | Biedermann et al. |
| 2003/0118395 A1 | 6/2003 | Abels et al. |
| 2003/0163133 A1 | 8/2003 | Altarac et al. |
| 2004/0024464 A1 | 2/2004 | Errico et al. |
| 2004/0102781 A1 | 5/2004 | Jeon |
| 2004/0116929 A1 | 6/2004 | Barker et al. |
| 2004/0127906 A1 | 7/2004 | Culbert et al. |
| 2004/0138662 A1 | 7/2004 | Landry et al. |
| 2004/0181224 A1 | 9/2004 | Biedermann et al. |
| 2004/0193160 A1 | 9/2004 | Richelsoph |
| 2004/0236330 A1 | 11/2004 | Purcell et al. |
| 2005/0021031 A1 | 1/2005 | Foley et al. |
| 2005/0033289 A1 | 2/2005 | Warren et al. |
| 2005/0131409 A1 | 6/2005 | Chervitz et al. |

(56) References Cited

U.S. PATENT DOCUMENTS

| | | |
|---|---|---|
| 2005/0131537 A1 | 6/2005 | Hoy et al. |
| 2005/0131538 A1 | 6/2005 | Chervitz et al. |
| 2005/0131545 A1 | 6/2005 | Chervitz et al. |
| 2005/0203515 A1 | 9/2005 | Doherty et al. |
| 2005/0203516 A1 | 9/2005 | Biedermann et al. |
| 2005/0228392 A1 | 10/2005 | Keyer et al. |
| 2005/0261687 A1 | 11/2005 | Garamszegi et al. |
| 2006/0004359 A1 | 1/2006 | Kramer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0015105 A1 | 1/2006 | Warren et al. |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0084981 A1 | 4/2006 | Shluzas |
| 2006/0111714 A1 | 5/2006 | Foley |
| 2006/0149240 A1 | 7/2006 | Jackson |
| 2006/0149241 A1 | 7/2006 | Richelsoph |
| 2006/0155277 A1 | 7/2006 | Metz-Stavenhagen |
| 2006/0161152 A1 | 7/2006 | Ensign et al. |
| 2006/0235392 A1 | 10/2006 | Hammer et al. |
| 2006/0241599 A1 | 10/2006 | Konieczynski et al. |
| 2006/0241600 A1 | 10/2006 | Ensign et al. |
| 2006/0241603 A1 | 10/2006 | Jackson |
| 2006/0276791 A1 | 12/2006 | Shluzas |
| 2007/0012387 A1 | 1/2007 | Wilzbacher et al. |
| 2007/0055241 A1 | 3/2007 | Matthis et al. |
| 2007/0093818 A1 | 4/2007 | Biedermann et al. |
| 2007/0093826 A1 | 4/2007 | Hawkes et al. |
| 2007/0118132 A1 | 5/2007 | Culbert et al. |
| 2007/0123868 A1 | 5/2007 | Culbert et al. |
| 2007/0161996 A1 | 7/2007 | Biedermann et al. |
| 2007/0161999 A1 | 7/2007 | Biedermann et al. |
| 2007/0219556 A1 | 9/2007 | Altarac et al. |
| 2007/0225712 A1 | 9/2007 | Altarac et al. |
| 2007/0225713 A1 | 9/2007 | Altarac et al. |
| 2007/0270813 A1 | 11/2007 | Garamszegi |
| 2008/0004625 A1 | 1/2008 | Runco et al. |
| 2008/0012581 A1 | 1/2008 | Schulz et al. |
| 2008/0015579 A1 | 1/2008 | Whipple |
| 2008/0024957 A1 | 1/2008 | Lee |
| 2008/0045953 A1 | 2/2008 | Garamszegi |
| 2008/0097436 A1 | 4/2008 | Culbert et al. |
| 2008/0125788 A1 | 5/2008 | Cohen et al. |
| 2008/0177322 A1 | 7/2008 | Davis et al. |
| 2008/0269809 A1 | 10/2008 | Garamszegi |
| 2009/0082775 A1 | 3/2009 | Altarac et al. |
| 2009/0171391 A1 | 7/2009 | Hutton et al. |
| 2009/0171392 A1 | 7/2009 | Garcia-Bengochea et al. |
| 2009/0326582 A1 | 12/2009 | Songer et al. |
| 2009/0326586 A1 | 12/2009 | Duarte |
| 2010/0137920 A1 | 6/2010 | Hammill |
| 2010/0145389 A1 | 6/2010 | Triplett et al. |
| 2010/0312279 A1 | 12/2010 | Gephart et al. |
| 2011/0022088 A1 | 1/2011 | Forton et al. |
| 2011/0040328 A1 | 2/2011 | Miller et al. |
| 2011/0071571 A1 | 3/2011 | Abdelgany |
| 2011/0093014 A1 | 4/2011 | Davis et al. |
| 2011/0098755 A1* | 4/2011 | Jackson ............ A61B 17/7008 606/305 |
| 2011/0152942 A1 | 6/2011 | Oh et al. |
| 2011/0270325 A1 | 11/2011 | Keyer et al. |
| 2012/0022597 A1 | 1/2012 | Gephart et al. |
| 2012/0041490 A1 | 2/2012 | Jacob et al. |
| 2012/0046700 A1 | 2/2012 | Jackson et al. |
| 2012/0179212 A1 | 7/2012 | Jackson |
| 2012/0209335 A1 | 8/2012 | Termyna |
| 2012/0265212 A1 | 10/2012 | Seek |
| 2012/0296380 A1 | 11/2012 | Simonson |
| 2013/0023941 A1 | 1/2013 | Jackson |

FOREIGN PATENT DOCUMENTS

| | | |
|---|---|---|
| DE | 19720782 | 12/2004 |
| EP | 1121902 | 9/2004 |
| EP | 1474050 | 11/2004 |
| EP | 1634537 | 11/2007 |
| EP | 1857064 | 11/2007 |
| EP | 1190678 | 6/2008 |
| EP | 1570795 | 8/2008 |
| EP | 1579816 | 6/2013 |
| FR | 2729291 | 7/1996 |
| FR | 2796545 | 1/2001 |
| FR | 2856578 | 12/2004 |
| FR | 2857850 | 1/2005 |
| FR | 2865373 | 7/2005 |
| FR | 2865375 | 7/2005 |
| FR | 2865377 | 7/2005 |
| FR | 2865378 | 7/2005 |
| GB | 2173104 | 10/1986 |
| GB | 2365345 | 2/2002 |
| WO | 0122893 | 4/2001 |
| WO | WO0122893 | 4/2001 |
| WO | 02054966 | 7/2002 |
| WO | 03068083 | 8/2003 |
| WO | 03068088 | 8/2003 |
| WO | 2004041100 | 5/2004 |
| WO | 2004089245 | 10/2004 |
| WO | 2004107997 | 12/2004 |
| WO | 2005000136 | 1/2005 |
| WO | 2005000137 | 1/2005 |
| WO | 2005020829 | 3/2005 |
| WO | 2005072632 | 8/2005 |
| WO | 2005082262 | 9/2005 |
| WO | 2005099400 | 10/2005 |
| WO | 2006012088 | 2/2006 |
| WO | 2006017616 | 2/2006 |
| WO | 2006028537 | 3/2006 |
| WO | 0149191 | 7/2007 |
| WO | 2012030712 | 3/2012 |

OTHER PUBLICATIONS

File history of U.S. Appl. No. 11/749,615, now U.S. Pat. No. 7,942,910, as of Nov. 27, 2013. Filing date, May 16, 2007. First Named Inventor, Robert L. Doubler. Title, Polyaxial Bone Screw.

File history of U.S. Appl. No. 12/355,145, now U.S. Pat. No. 7,947,065, as of Nov. 27, 2013. Filing date, Jan. 16, 2009. First Named Inventor, John E. Hammill. Title, Locking Polyaxial Ball and Socket Fastener.

File history of U.S. Appl. No. 12/700,436, now U.S. Pat. No. 7,951,173, as of Nov. 27, 2013. Filing date, Feb. 4, 2010. First Named Inventor, John E. Hammill. Title, Pedicle Screw Implant System.

File history of U.S. Appl. No. 12/833,751, now U.S. Pat. No. 8,075,603, as of Nov. 27, 2013. Filing date, Jul. 9, 2010. First Named Inventor, John E. Hammill. Title, Locking Polyaxial Ball and Socket Fastener.

File history of U.S. Appl. No. 13/317,969, as of Nov. 27, 2013. Filing date, Nov. 1, 2011. First Named Inventor, Roger P. Jackson. Title, Polyaxial Bone Anchor With Pop-on Shank and Pivotable Retainer.

International Searching Authority, "International Preliminary Report on Patentability," for Int. App. No. PCT/US2014/036028, mailed on Nov. 12, 2015, pp. 1-7.

* cited by examiner

BOTTOM-LOADING ANCHOR ASSEMBLY

DESCRIPTION OF EMBODIMENTS

Figures 1, 2:
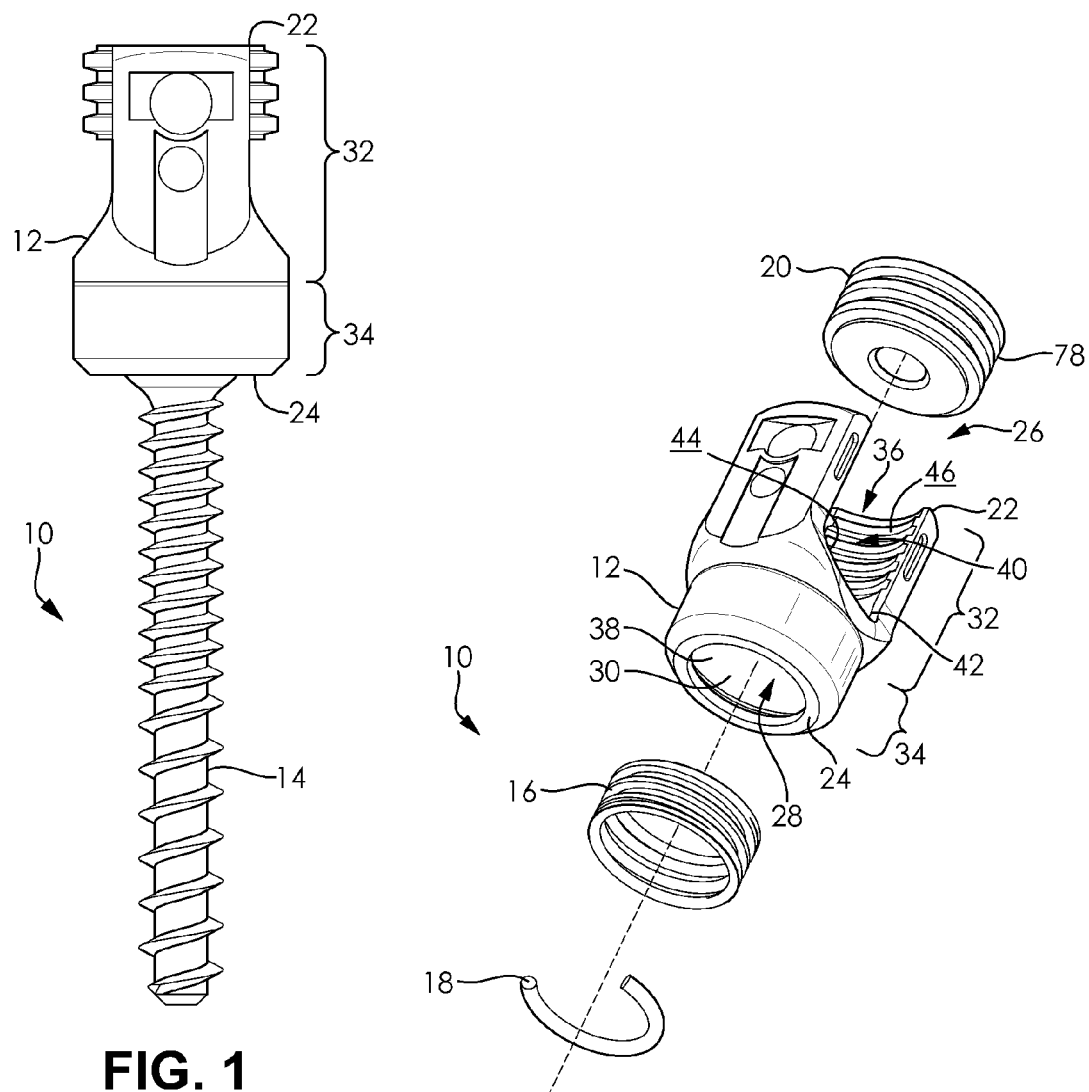
FIG. 1 illustrates an embodiment of a bottom-loading anchor assembly.
FIG. 2 is an exploded perspective view of the anchor assembly illustrated in FIG. 1.
Figure 3:
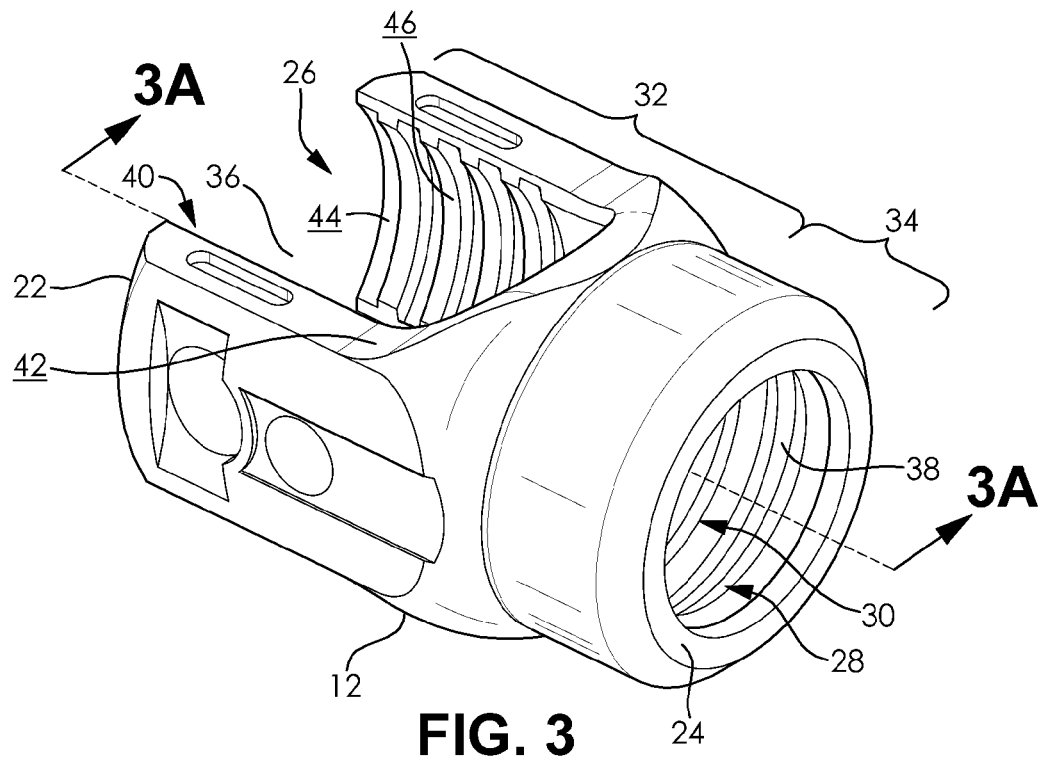
FIG. 3 is a perspective view of the head member of the anchor assembly illustrated in FIG. 1 with an associated compression member and retaining member.
Figure 3A:
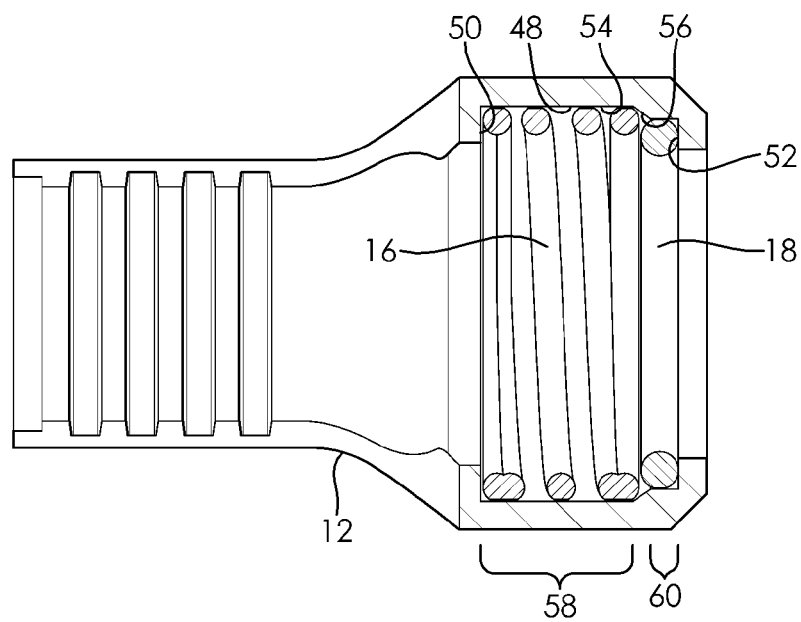
FIG. 3A is a sectional view of FIG. 3, taken along line 3A-3A.

The following detailed description and the appended drawings describe and illustrate various example embodiments. The description and illustration of these examples are provided to enable one skilled in the art to make and use an anchor tower. They are not intended to limit the scope of the claims in any manner.

As used herein, the term "bottom-loading" refers to an ability of a proximal end of an anchor of an anchor assembly to be inserted into an opening defined by an end of a head member of the anchor assembly through which the anchor is disposed in the fully assembled anchor assembly. It does not preclude an ability of a proximal end of an anchor of an anchor assembly to be inserted through an opening defined by an end of a head member of the anchor assembly that is opposite an opening defined by an end of a head member of the anchor assembly through which the anchor is disposed in the fully assembled anchor assembly.

As used herein, the terms "top" and "bottom" refer to opposite portions of a body relative to each other. Neither term requires any specific positioning of the member to which the terms apply relative to any other item.

As used herein, the term "channel" refers to a recess in a surface. The term does not require any particular cross-sectional shape of the recess with respect to a lengthwise axis of the channel or a portion of the channel. The term does not require any particular lengthwise configuration, either. Non-limiting examples of lengthwise configurations that can be used for the channels described herein include linear, curvilinear, segmented linear, and tortuous paths. The term does not require any particular length relative to another component of an anchor assembly, either. For example, a channel defined by a head member of an anchor assembly can have any suitable length relative to the head member. Non-limiting examples of channel lengths relative to a head member of an anchor assembly include circumferential, i.e., a channel that extends along an entire circumference on a surface of a head member, such as along an entire circumference on an inner surface of a head member; and partial circumferential, i.e., a channel that extends along only a portion of a circumference on a head member. In this context, the term "circumference" refers to a curved geometric shape on a surface, including, but not limited to, a circular shape.

As used herein, the term "ramp" refers to a surface that transitions from a first surface at a distance from a reference point to second surface at a different distance from a reference point. The term does not require the surface to be on a plane that lies at any particular angle with respect to the first and second surfaces between which it transitions. Accordingly, the surface can be on a plane that lies at any angle with respect to the first and second surfaces between which it transitions. Non-limiting examples of angles at which a plane containing a ramp described herein can lie with respect to one or both of the surfaces between which the ramp transitions include acute angles, obtuse angles, right angles, and substantially right angles. The term also does not require the surface to have any particular length, width or other dimension.

Each of FIGS. 1, 2, 3, 3A, 4, 4A, 4B, 4C, 5A, and 5B illustrates an anchor assembly 10 or one or more components thereof. The anchor assembly 10 comprises a head member 12 and an anchor 14. A compression member 16 and a retaining member 18 are disposed within the head member 12 and a cap 20 is releasably connected to the head member 12. In the fully assembled anchor assembly 10, the anchor 14 is partially disposed within the head member 12.

The head member 12 has a proximal end 22, which can be referred to as the "top" of the head member 12, and a distal end 24, which can be referred to as the "bottom" of the head member 12. The head member 12 defines a proximal opening 26 at the proximal end 22 and a distal opening 28 at the distal end 24. A passageway 30 extends from the proximal opening 26 to the distal opening 28 along the length of the head member 12. The head member 12 includes a proximal portion 32 and a distal portion 34. The proximal portion 32 defines a proximal chamber 36 of the passageway 30 and the distal portion 34 defines a distal chamber 38 of the passageway 30. Each of the proximal portion 32 and the distal portion 34 has a width extending on an axis orthogonal to a lengthwise axis extending from the proximal end 22 to the distal end 24 of the head member 12. In the illustrated embodiment, the proximal portion 32 has a width that is greater than a width of the distal portion 34. A head member can be configured with an opposite arrangement, i.e., with a distal portion having a width greater than a width of its proximal portion. Also, a head member can be configured with a proximal portion having a width that is the same as or substantially the same as a width of its distal portion.

The proximal portion 32 of the head member 12 defines a lateral opening 40. In the illustrated embodiment, the lateral opening 40 is continuous with the proximal opening 26 and is bounded by a u-shaped wall 42 of the head member. The lateral opening 40 can have any suitable size, shape and configuration, each of which can be based upon the size, shape and configuration of a member intended to be secured by the head member 40. The lateral opening 40 of the illustrated embodiment is suitable for use with a rod. Non-limiting examples of alternative shapes for the lateral opening 40 include v-shaped, rectangular shaped, square-shaped, curvilinear, linear, and segmented linear. A non-limiting example of an alternative configuration for the lateral opening 40 is an opening that is separate and distinct from the proximal opening 26.

While not illustrated in the Figures, the proximal portion 32 can define a second lateral opening if it is desirable to allow a member that will be secured by the head member 12 to extend away from the head member 12 in two directions. For example, if it is desirable to allow a rod to be secured by the head member in a manner in which the rod extends away from the head member in two directions, the head member 40 can define a second lateral opening. If included, a second lateral opening can be oriented on the head member in any desirable position relative to the first lateral opening 40. For example, a second lateral opening can be positioned opposite the first lateral opening 40 relative to a lengthwise axis extending from the proximal end 22 to the distal end 24 of the head member 12. Alternatively, the second lateral opening can be positioned at an angle to the first lateral opening 40 relative a lengthwise axis extending from the proximal end 22 to the distal end 24 of the head member 12. In these embodiments, any suitable angle can be used, included an orthogonal angle, a substantially orthogonal angle, an acute angle, and an obtuse angle.

Also, if included, a second lateral opening can have the same size, shape and configuration as those of the first lateral opening 40. Alternatively, a second lateral opening can have a different size, and/or a different shape, and/or a different configuration than those of the first lateral opening 40.

The proximal portion 32 of the head member 12 has an inner surface 44. The inner surface 44 can define structure that provides a desired functionality. For example, in the illustrated embodiment, the inner surface 44 defines a threaded surface 46 that mates with a threaded surface 78 of the cap 20 for securing the cap 20 to the head member 12. Other non-limiting examples of structure that can be defined by the inner surface 44 include one or more projections that facilitate retention of a member secured by the head member 12. Alternatively, the inner surface 44 can comprise a smooth or substantially smooth surface that is free of projections or other functional structure.

The proximal portion 32 can define additional openings, notches and/or other additional structure as desired.

The distal portion 34 of the head member 12 has an inner surface that defines a channel 48. The channel 48 is in communication with the passageway 30 and, as described in detail below, is sized and configured to receive the compression member 16 and the retaining member 18 and to allow these components to function as described below. In the illustrated embodiment, the channel 48 is a circumferential channel that extends along a circular shape on the inner surface. As best illustrated in FIGS. 3A, 4A, 4B, and 4C, the channel 48 is bounded by first 50 and second 52 lateral walls and base wall 54. Base wall 54 defines a ramp 56, giving the channel 48 a proximal portion 58 having a first depth and a distal portion 60 having a second depth that is less than the first depth. The ramp 56 defines a transition between the proximal 58 and distal 60 portions.

In the illustrated embodiment, the ramp 56 comprises a circumferential ramp that extends along a circular shape on the inner surface of the distal portion 34 of the head member 12. Alternatively, a partial circumferential ramp can be used. In the illustrated embodiment, the ramp 56 lies on a plane that is disposed at an acute angle to the portion of the base wall 54 that is disposed in the distal portion 60 of the channel 48 and at an obtuse angle to the portion of the base wall 54 that is disposed in the proximal portion 58 of the channel 48. This configuration facilitates movement of the retaining member 18 away from and toward the distal portion 60 of the channel 48, as described below.

The anchor 14 is an elongate member having a head 62 and a shank 64. In the illustrated embodiment, the head 62 is a spherical body with a flattened proximal surface 66 that defines a recess 68. The head 62 has an apex 70 at the axial portion that defines the maximum outer diameter of the spherical body. The shank 64 defines a helical plane 72 that facilitates securement of the anchor 14 to a member, such as a bone or a member formed of another material, such as wood or plastic. In the illustrated embodiment, the helical plane 72 has a proximal portion 74 with a first pitch and a distal portion 76 with a second pitch. It is noted that the anchor 14 can include a shank having any suitable structure that allows the anchor 14 to perform as described herein. Inclusion of a helical plane is considered optional. Non-limiting examples of other suitable structures that can be defined by the shank of the anchor include a nail-like structure and a barbed member. Similarly, the anchor 14 can include a head having any suitable structure that allows the anchor 14 to perform as described herein. Non-limiting examples of other suitable structures include a spherical body, a cube, and a block.

The compression member 16 is disposed within the proximal portion 58 of channel 48, proximal to the retaining member 18. In the illustrated embodiment, the compression member 16 comprises a coil spring. Any suitable compression member can be used, however. The compression member need only be able to allow the retaining member 18 to move in a first direction within the channel 48 and to effect movement of the retaining member 18 in a second, opposite or substantially opposite direction within the channel 48, as described below. Non-limiting examples of suitable compression members include helical springs, wave springs, and bushings. The compression member can be formed of any suitable material, including metal, plastic, and elastomeric materials. In the illustrated embodiment, the compression member 16 has a cross-sectional diameter that is less than a cross-sectional diameter of the retaining member 18.

The retaining member 18 is disposed within the distal portion 60 of the channel 48, distal to the compression member 16. In the illustrated embodiment, the retaining member 18 comprises a C-shaped member having a resting diameter that is greater than an inner diameter of the distal portion 34 of the head member 12 within the distal portion 60 of the channel 48. This provides the retaining member 18 with a radially compressed configuration and a radially expanded configuration. With this configuration, the retaining member 18 expands in a radially outward manner as the retaining member 18 moves from the distal portion 60 of the channel 48 to the proximal portion 58 of the channel 48. The retaining member 18 can have any suitable configuration, however. For example, retaining member 18 can alternatively have a semi-circular configuration or an annular configuration. The retaining member 18 need only be able to expand radially outward as it transitions from the distal portion 60 of the channel 48 to the proximal portion 58 of the channel 48. The compression member can be formed of any suitable material, including metal, plastic, and elastomeric materials. Also, the retaining member 18 can have any suitable cross-sectional shape, including circular, ovoid, and any other cross-sectional shape. In the illustrated embodiment, the retaining member 18 has a cross-sectional diameter that is greater than a cross-sectional diameter of the compression member 16.

In the illustrated embodiment, the compression member 16 and the retaining member 18 comprise distinct components. It is noted, however, that a single component that includes both a compression member and a retaining member can be used, however. For example, the illustrated compression member 16 and retaining member 18 could be secured to each other to provide a single component that includes both a compression member and a retaining member. Furthermore, it is noted that each of these components, can comprise a portion of another component. For example, in embodiments that include an insert positioned within the head assembly, such as the embodiments described below, a compression member can comprise a distal portion of the insert. A compression member could even be secured a head of an anchor in an embodiment.

The cap 20 is releasably connected to the head member 12. In the illustrated embodiment, the cap 20 defines a threaded surface 78 that mates with a threaded surface 46 of the inner surface 44 of the proximal portion 32 of the head member 12. It is noted, though, that the cap 20 can include any suitable structure that enables it to be releasably secured to the head member 12. Non-limiting examples of suitable structure includes projections, magnets and other structure suitable for securing a cap to a body. Inclusion of a cap is considered optional.

Figure 4:
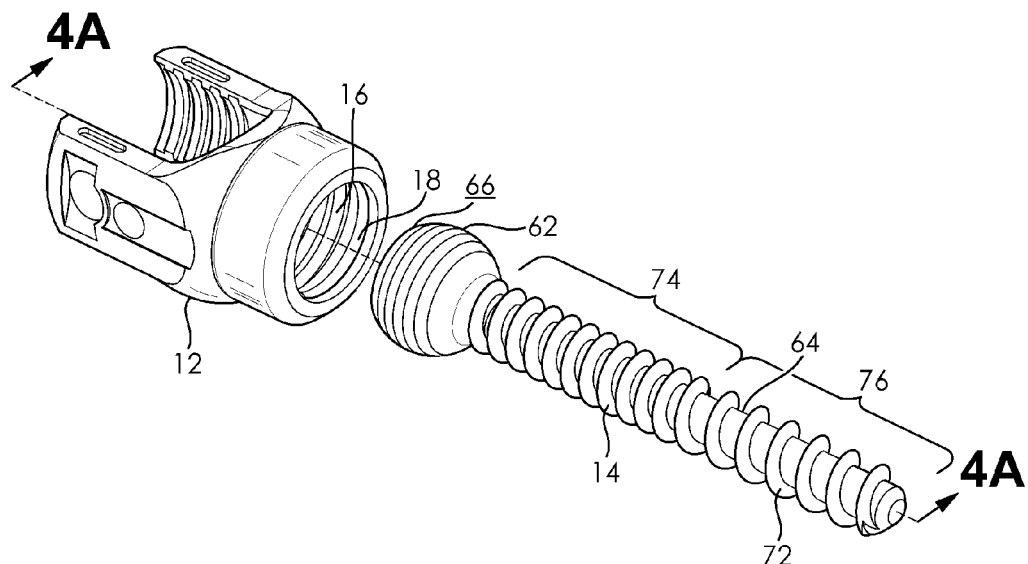
FIG. 4 is an exploded perspective view of the anchor assembly illustrated in FIG. 1.
Figure 4A:
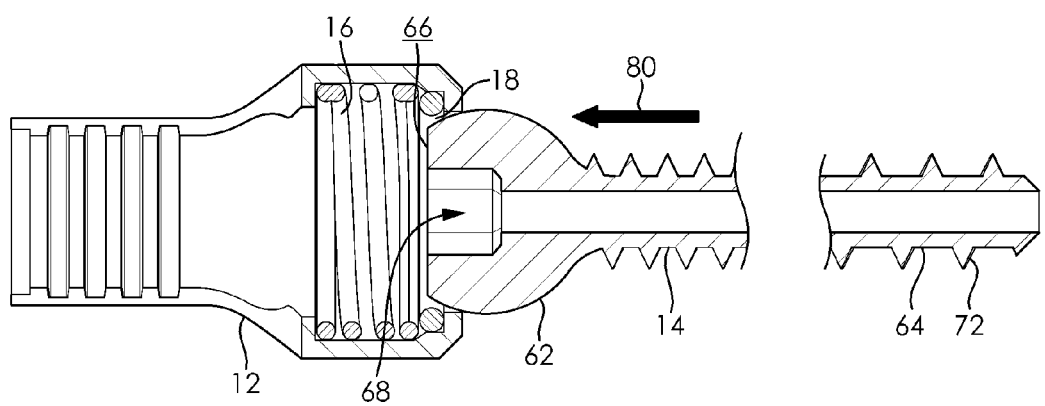
FIG. 4A is a magnified partial sectional view of the anchor assembly illustrated in FIG. 1. The anchor is shown in a first position within the head member.
Figure 4B:
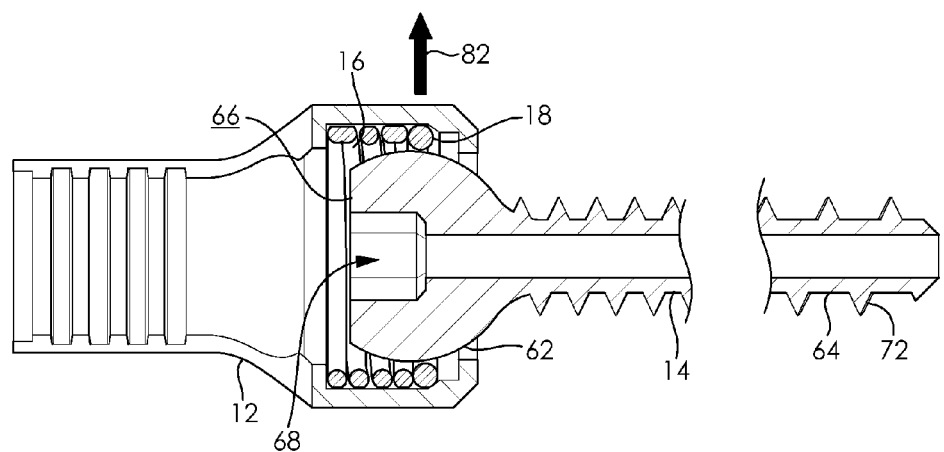
FIG. 4B is a magnified partial sectional view of the anchor assembly illustrated in FIG. 1. The anchor is shown in a second position within the head member.
Figure 4C:
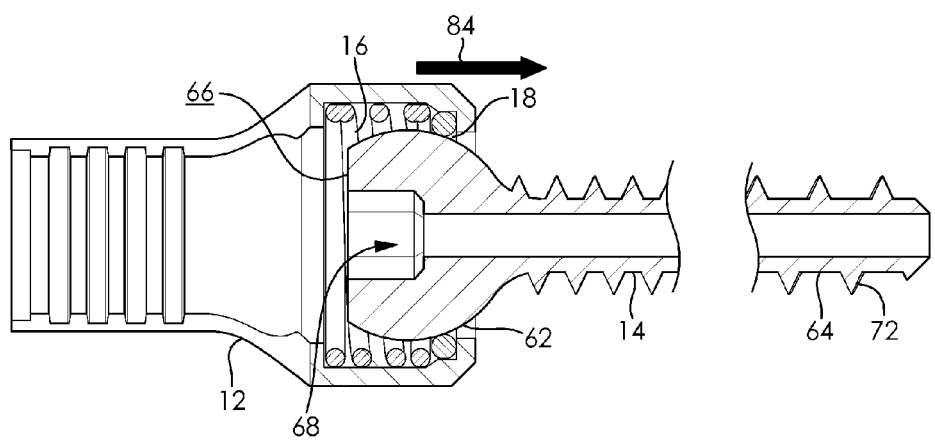
FIG. 4C is a magnified partial sectional view of the anchor assembly illustrated in FIG. 1. The anchor is shown in a third position within the head member.

FIGS. 4A, 4B, and 4C illustrate movement of the compression member 16 and the retaining member 18 as the head 62 of the anchor 14 is moved into the distal opening 28 of the head member 12. FIG. 4A illustrates proximally-directed movement, represented by arrow 80, of the head 62 of the anchor 14 into the distal portion 34 of the head member 12 and the distal chamber 38 of the passageway 30. In the position illustrated in FIG. 4A, the apex 70 of the head 62 of the anchor 14 is distal to the distal portion 60 of the channel 48. As a result, compression member 16 is maintaining retaining member 18 in the distal portion 60 of the channel 48.

FIG. 4B illustrates radially-outward movement of the retaining member 18, represented by arrow 82, that occurs as the apex 70 of the head 62 of the anchor 14 enters the distal portion 60 of the channel 48. As proximally-directed movement of the head 62 of the anchor 14 continues, the apex 70 engages the retaining member 18 and moves it toward the proximal portion 58 of the channel 48, along the ramp 56. As the retaining member 18 moves in this manner, it expands radially outwardly.

FIG. 4C illustrates distally-directed movement of the retaining member 18, represented by arrow 84, that occurs as the apex 70 of the head 62 of the anchor 14 passes the retaining member 18 proximally and enters the proximal portion 58 of the channel 48. In the illustrated embodiment, the compression member 16 maintains a distally-directed compressive force on the retaining member 18. Accordingly, once the apex 70 reaches a sufficient position on a lengthwise axis of the head member 12, the distal portion 60 of the channel 48 provides sufficient space to accommodate the retaining member 18 and the compressive force provided by the compression member 16 moves the retaining member distally along the ramp 56 and, ultimately back into the distal portion 60 of the channel 48. Once this occurs, as illustrated in FIG. 4C, the head member 12 forces the retaining member 18 to adopt its non-expanded configuration, which prevents the head 62 of the anchor 14 from exiting the head member 12, effectively securing the head 62 of the anchor 14 in the head member 12.

Figure 5A:
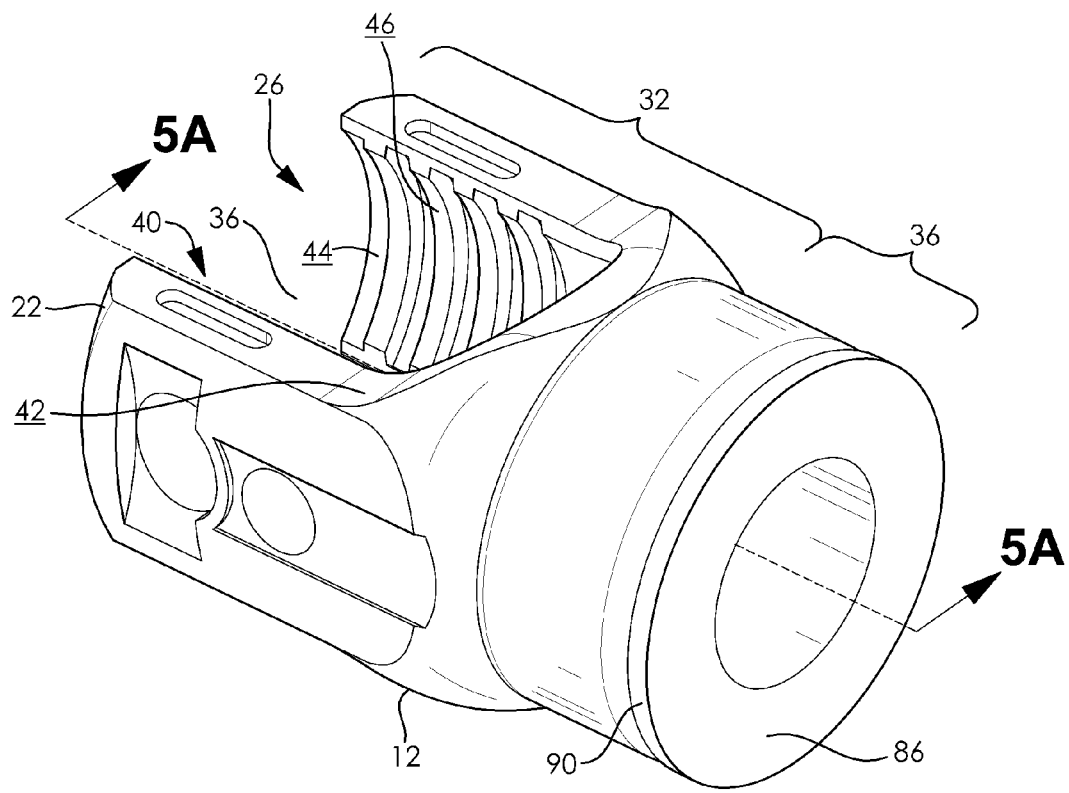
FIG. 5A is a perspective view of the head member of the anchor assembly illustrated in FIG. 1 with a plug.
Figure 5B:
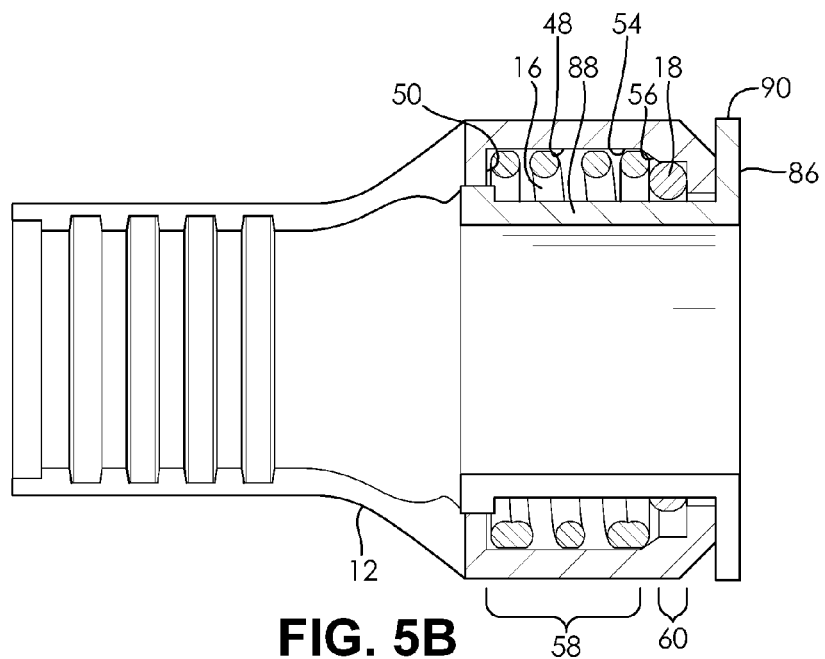
FIG. 5B is a sectional view of the head member of the anchor assembly illustrated in FIG. 1 with an associated compression member and retaining member and a plug disposed within the head member.

FIGS. 5A and 5B illustrate an optional plug 86 that is releasably secured to the distal portion 34 of the head member 12 prior securing an anchor 14 to the head member 12. The plug 86 defines a body 88 that can be passed through the distal opening 28 and that extends proximally beyond the channel 48. A flange 90 remains external to the head member 12. When secured to the head member 12 in this manner, the plug 86 provides a barrier that blocks access to the compression member 16 and the retaining member 18.

Figure 6:
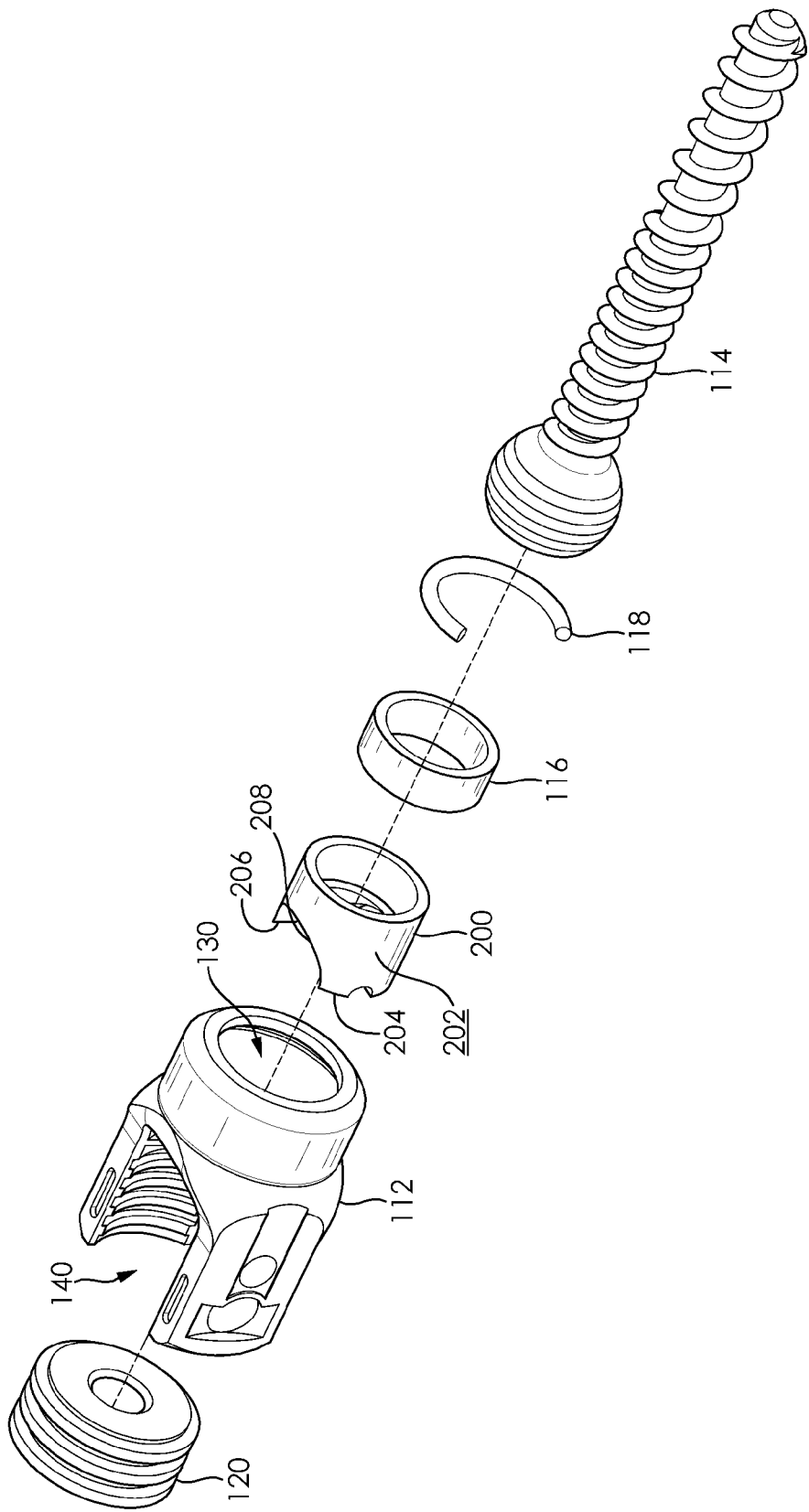
FIG. 6 is an exploded view of another embodiment of a bottom-loading anchor assembly.
Figure 7A:
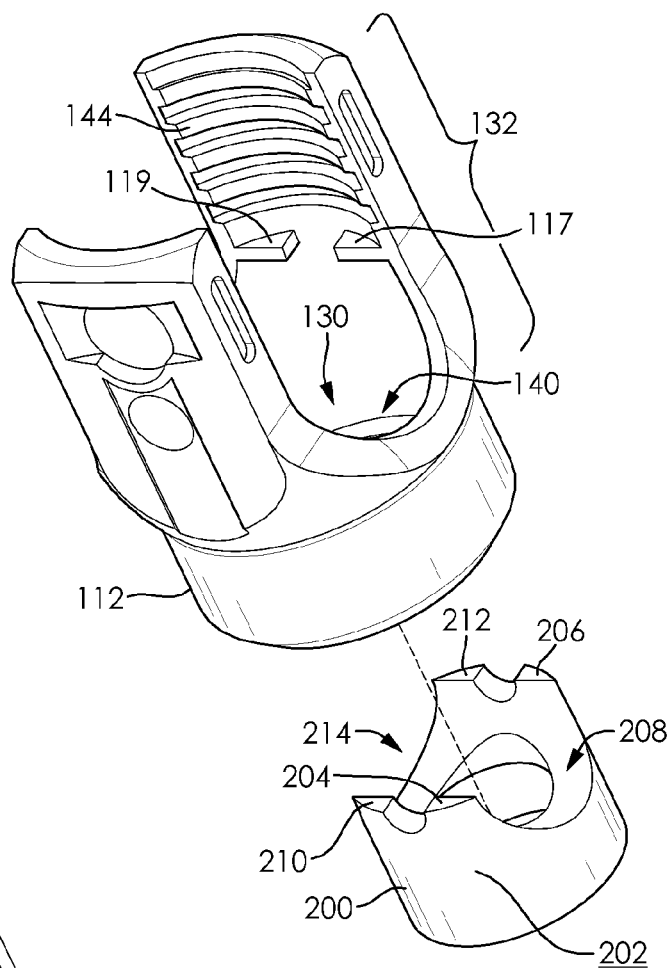
FIG. 7A is an exploded view of the head member and insert of the anchor assembly illustrated in FIG. 6.
Figure 7B:
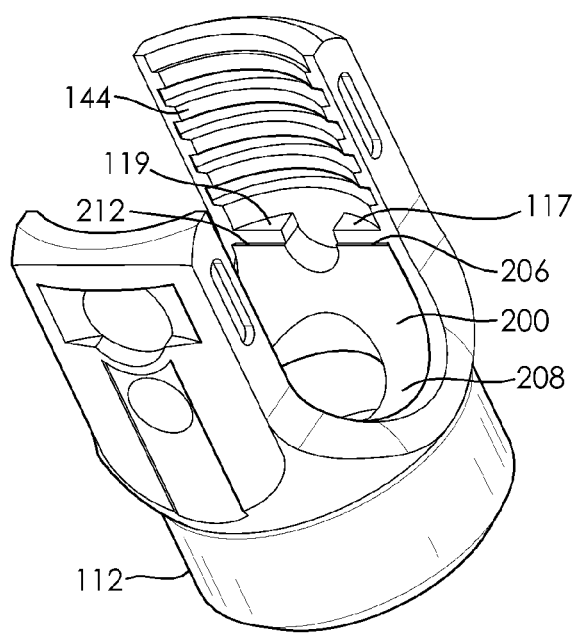
FIG. 7B is a perspective view of the head member and insert illustrated in FIG. 7A.

Each of FIGS. 6, 7A and 7B illustrates another anchor assembly 110 or one or more components thereof. The illustrated anchor assembly 110 is similar to the anchor assembly 10 illustrated in FIGS. 1 and 2 and described above, except as described below. Thus, the anchor assembly 110 comprises a head member 112 and an anchor 114. A compression member 116 and a retaining member 118 are disposed within the head member 112 and a cap 120 is releasably connected to the head member 112. In the fully assembled anchor assembly 110, the anchor 114 is partially disposed within the head member 112.

In this embodiment, the compression member 116 comprises a ring member formed of a compressible material. The compression member 116 is sufficiently compressible to enable the compression member 116 to function as described above in connection with the anchor 10 illustrated in FIGS. 1 and 2. As such, the compression member 116 can be formed of any suitable material that provides a suitable level of compressibility. Non-limiting examples of suitable materials include elastomeric materials and rubber materials.

In this embodiment, the anchor assembly 110 includes an insert 200 that is disposed within the passageway 130 of the head member 112. The insert 200 has a circumferential wall 202 that defines first 204 and second 206 stanchions and a notch 208 that extends between the stanchions 204, 206. In the illustrated embodiment, the notch 208 has a semi-circular shape that extends along the circumferential wall 202, but any shape can be used. A shape that compliments an outer surface of a member adapted to be secured by the head member 112, such as a rod, can be used. Accordingly, non-limiting examples of suitable shapes for the notch include semi-circular, arcuate, u-shaped, v-shaped, and rectangular-shaped, square-shaped. Also, a shape that is the same as or similar to the shape of the lateral opening 140 of the head member 112 is suitable.

As best illustrated in FIG. 7A, the insert 200 can define third 210 and fourth 212 stanchions and a second notch 214 that extends between the third 210 and fourth 212 stanchions. If included, a second notch can be oriented on the insert 200 in any desirable position relative to the first notch 208. For example, as illustrated in FIG. 7A, a second notch 214 can be positioned opposite the first notch 208 relative to a lengthwise axis of the insert 200. Alternatively, the second notch 214 can be positioned at an angle to the first notch 208 relative a lengthwise axis of the insert 200. In these embodiments, any suitable angle can be used, included an orthogonal angle, a substantially orthogonal angle, an acute angle, and an obtuse angle.

Also in this embodiment, as best illustrated in FIG. 7B, the inner surface 144 of the proximal portion 132 of the head member 112 defines projections 216, 218 that provide mechanical stops to proximal movement of the insert 200 within the passageway 130 of the head member 112. Any suitable number of projections can be included, including two, as illustrated, one, three, four or more. While not visible in the Figures, the illustrated embodiment includes four projections, which is equal to the number of stanchions defined by the insert.

Figure 8A:
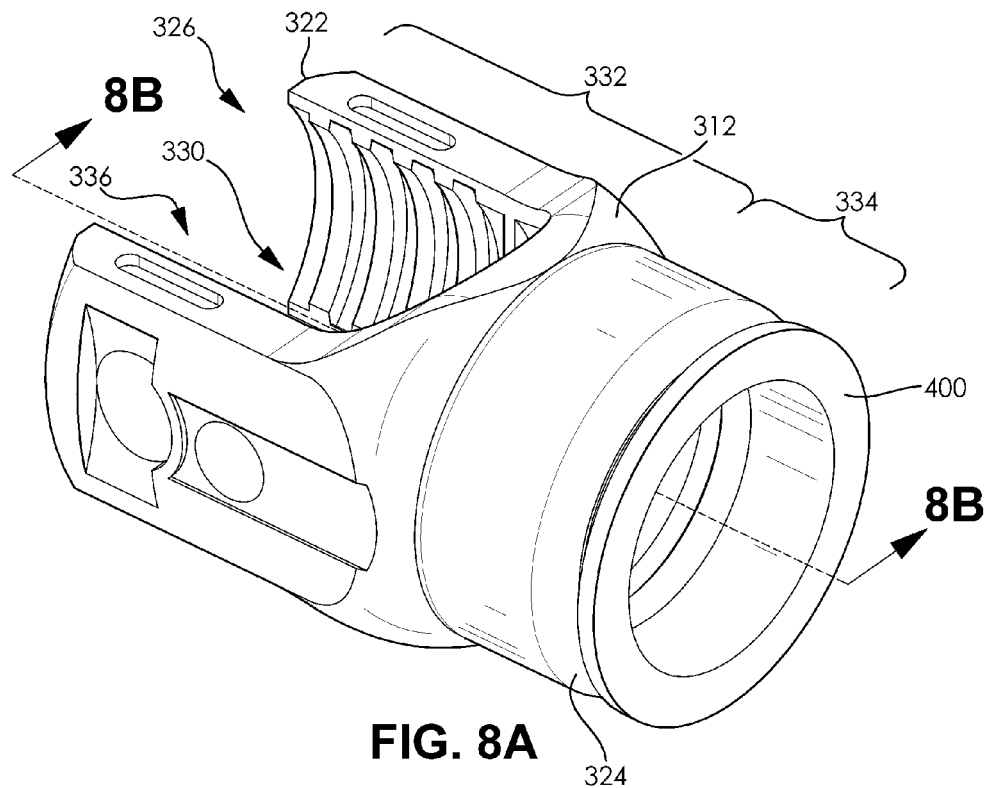
FIG. 8A is a perspective view of another head member with an associated compression member and retaining member.
Figure 8B:
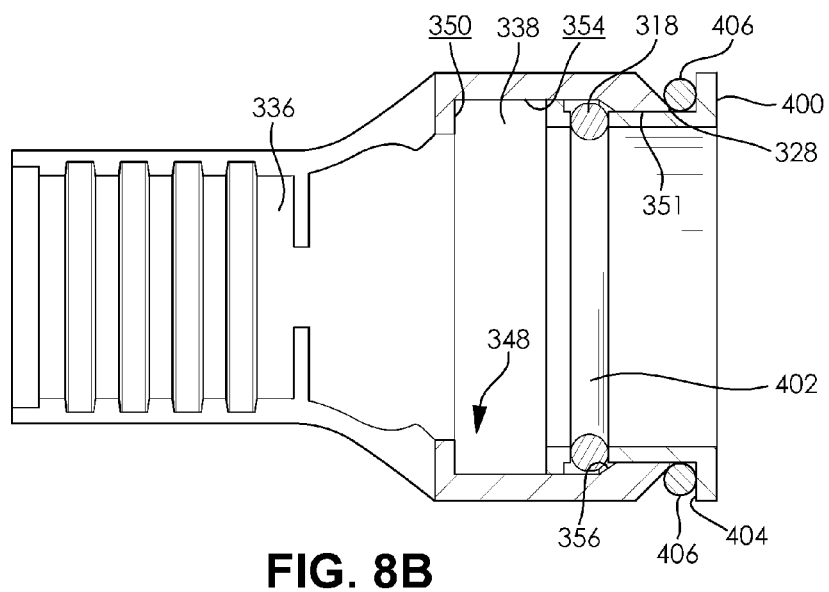
FIG. 8B is a sectional view of FIG. 8A, taken along line 8B-8B.

Each of FIGS. 8A and 8B illustrates a head member 312 useable as a component of an anchor assembly, and an associated retaining member 318. The illustrated head member 312 is similar to the head member 12 illustrated in FIGS. 1 and 2 and described above. Thus, the head member 312 has a proximal end 322 and a distal end 324, a proximal opening 326 at the proximal end 322 and a distal opening 328 at the distal end 324. A passageway 330 extends from the proximal opening 326 to the distal opening 328 along the length of the head member 312. The head member 312 includes a proximal portion 332 and a distal portion 334. The proximal portion 332 defines a proximal chamber 336 of the passageway 330 and the distal portion 334 defines a distal chamber 338 of the passageway 330. The distal portion 334 of the head member 312 has an inner surface that defines a channel 348 in communication with the passageway 330. In this embodiment, channel 348 is bounded by first lateral wall 350, circumferential surface 351, and base wall 354. Base wall 354 defines a ramp 356, giving the channel 348 a proximal portion 358 having a first depth and a distal portion 360 having a second depth that is less than the first depth. The ramp 356 defines a transition between the proximal 358 and distal 360 portions.

In this embodiment, a sleeve 400 eliminates the need for a compression member within the head member 312. The retaining member 318 is disposed within a slot 402 defined by sleeve 400. Sleeve 400 also defines a flange 404. A compression member 406 is disposed on the sleeve 400 between the flange 404 and the distal end 324 of the head member 312. Positioned in this manner, the compression member 406 allows the sleeve 400 to be moved proximally with respect to the head member 312. As the sleeve 400 is moved in this manner, the retaining member 318 moves from the distal portion 360 of the channel 348 to the proximal portion 358 of the channel 348, expanded radially outwardly in the process. Thus, when the sleeve 400 is moved proximally by a sufficient amount with respect to the head member 312, the retaining member 318 adopts its expanded configuration within the channel 348, which permits an anchor to be inserted into the head member 312 as described above. Then, distally-directed movement of the sleeve 400, produced by compression member 406 following release of a pushing force on the sleeve 400, returns the retaining member to the distal portion 360 of the channel 348, effectively securing the anchor to the head member 312.

Figure 9A:
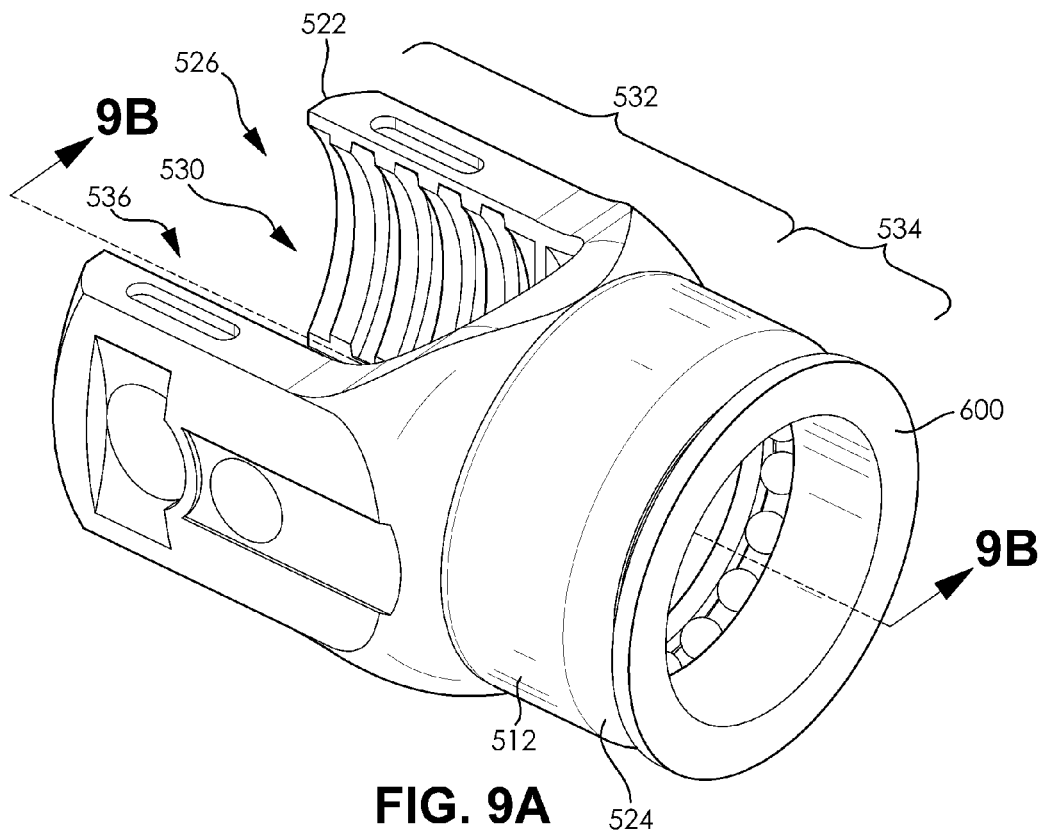
FIG. 9A is a perspective view of another head member with an associated compression member and retaining member.
Figure 9B:
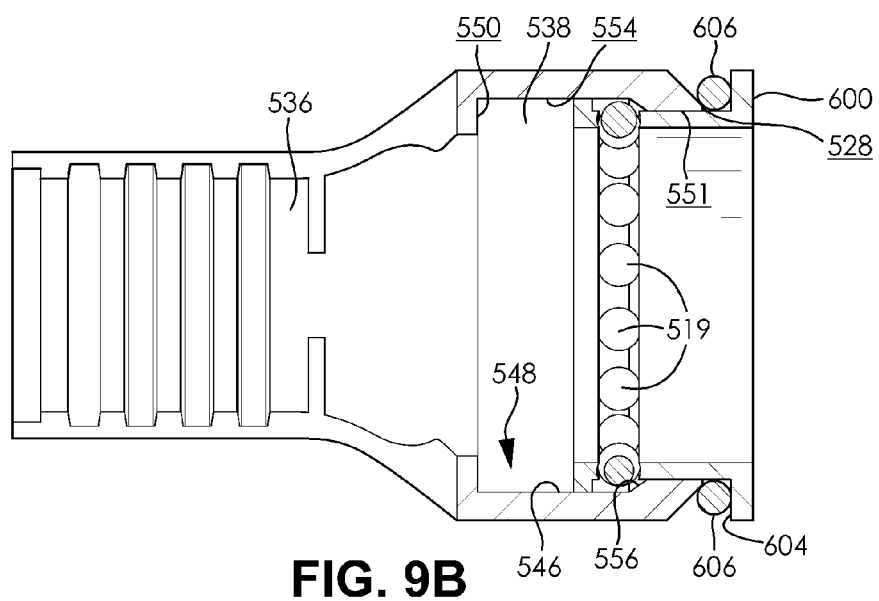
FIG. 9B is a sectional view of FIG. 9A, taken along line 9B-9B.

Each of FIGS. 9A and 9B illustrates a head member 512 useable as a component of an anchor assembly. The illustrated head member 512 is similar to the head member 12 illustrated in FIGS. 1 and 2 and described above. Thus, the head member 512 has a proximal end 522 and a distal end 524, a proximal opening 526 at the proximal end 522 and a distal opening 528 at the distal end 524. A passageway 530 extends from the proximal opening 526 to the distal opening 528 along the length of the head member 512. The head member 512 includes a proximal portion 532 and a distal portion 534. The proximal portion 532 defines a proximal chamber 536 of the passageway 530 and the distal portion 534 defines a distal chamber 538 of the passageway 530. The distal portion 534 of the head member 512 has an inner surface 546 that defines a channel 548 in communication with the passageway 530. In this embodiment, channel 548 is bounded by first lateral wall 550, circumferential surface 551, and base wall 554. Base wall 554 defines a ramp 556, giving the channel 548 a proximal portion 558 having a first depth and a distal portion 560 having a second depth that is less than the first depth. The ramp 556 defines a transition between the proximal 558 and distal 560 portions.

Similar to the embodiment illustrated in FIGS. 8A and 8B, a sleeve 600 eliminates the need for a compression member within the head member 512. In this embodiment, however, a plurality of ball bearings 519 is used in place of the expandable retaining member of the embodiments described above. The ball bearings 519 are disposed within a groove 620 defined by sleeve 600. Sleeve 600 also defines a flange 604. A compression member 606 is disposed on the sleeve 600 between the flange 604 and the distal end 624 of the head member 612. The compression member 606 allows the sleeve 600 to be moved proximally with respect to the head member 512. As the sleeve 600 is moved in this manner, the ball bearings 519 move from the distal portion 560 of the channel 548 to the proximal portion 558 of the channel 548. Thus, when the sleeve 600 is moved proximally by a sufficient amount with respect to the head member 512, the ball bearings 519 can be moved outwardly with respect to a longitudinal axis of the head member 512, which permits an anchor to be inserted into the head member 512 as described above. Then, distally-directed movement of the sleeve 600, produced by compression member 606 following release of a pushing force on the sleeve 600, returns the ball bearings 519 to the distal portion 560 of the channel 548, effectively securing the anchor to the head member 512.

While a plurality of ball bearings 519 is described and illustrated, it is understood that any suitable number of ball bearings can be used, including one ball bearing, two ball bearings, three ball bearings, or more. Indeed, the number of ball bearings included need only be at least one ball bearing.

Figure 10:
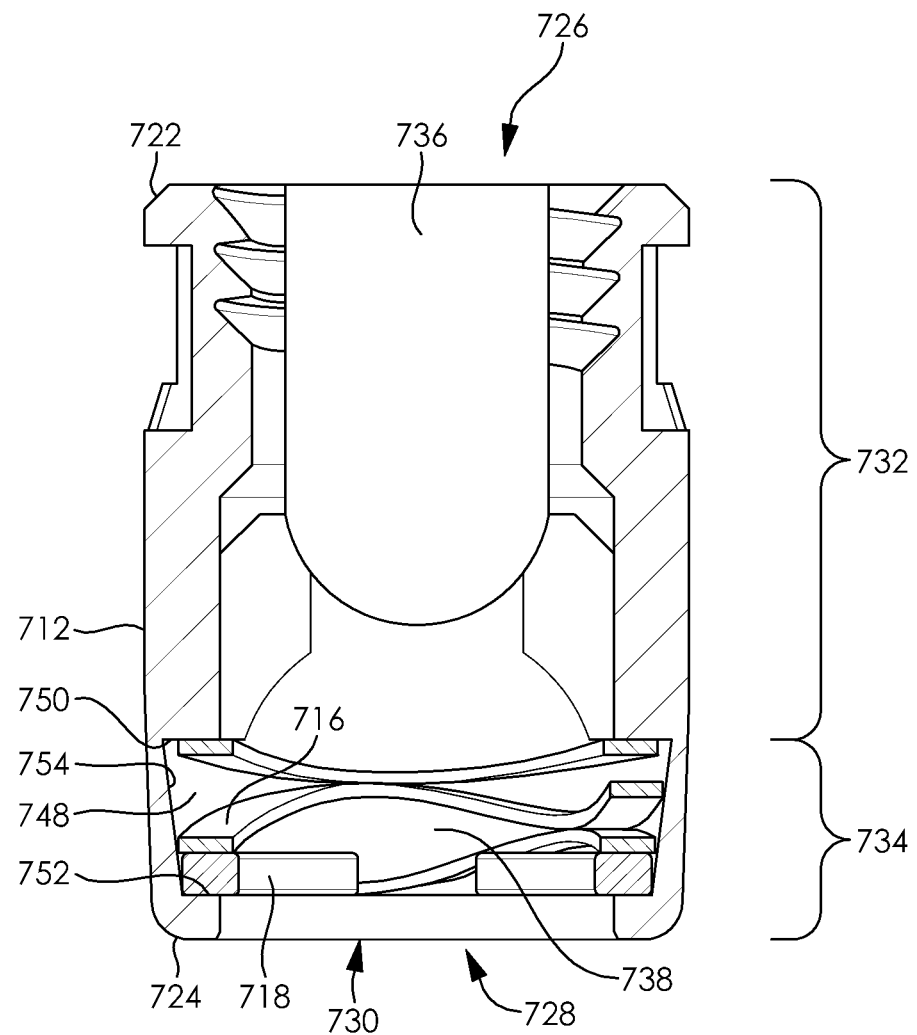
FIG. 10 is a sectional view of another head member with an associated compression member and retaining member.

FIG. 10 illustrates a head member 712 useable as a component of an anchor assembly. The illustrated head member 712 has a proximal end 722 and a distal end 724, a proximal opening 726 at the proximal end 722 and a distal opening 728 at the distal end 724. A passageway 730 extends from the proximal opening 726 to the distal opening 728 along the length of the head member 712. The head member 712 includes a proximal portion 732 and a distal portion 734. The proximal portion 732 defines a proximal chamber 736 of the passageway 730 and the distal portion 734 defines a distal chamber 738 of the passageway 730. The distal portion 734 of the head member 712 defines a channel 748 in communication with the passageway 730.

In this embodiment, a compression member 716 and a retaining member 718 are disposed within the channel 748 of the head member 712. Compression member 716 comprises a wave spring. A wave spring comprises one or more loops of flat wire with one or more waves in the loop. In embodiments using a wave spring as the compression member, any suitable type of wave spring can be used, including single-turn, multi-turn and nested wave springs. A single turn wave spring comprises a single such loop while a multi-turn wave spring comprises two or more such loops stacked with their waves extending in opposing directions.

In the illustrated embodiment, compression member 716 comprises a multi-turn wave spring comprising three loops. A nested wave spring comprises two or more such loops stacked with their waves extending in the same directions. Use of a wave spring as the compression member in an embodiment may provide a lower work height than that of a coil spring or other compression member, while providing the same force.

In this embodiment, channel 748 is bounded by first lateral wall 750, second lateral wall 752, and base wall 754. Base wall 754 defines a sloped surface extending between the first lateral wall 750 and the second lateral wall 752. In the illustrated embodiment, the base wall 754 is a frusto-conical surface, making channel 748 a circumferential channel without a ramp. It is noted that a channel having a partial-circumferential or other channel configuration in which a base wall comprises a sloped surface extending between a first lateral wall and a second lateral wall, or any two surfaces, could also be used. In use, the retaining member 718 moves expands radially outwardly as it is moved proximally within the channel, and contracts radially inwardly as it is moved distally within the channel.

The anchor assemblies are useful for connecting structures to each other. An anchor assembly according to an embodiment can be used to connect a structure to which the anchor of the anchor assembly is attached with another structure that can be secured by the head member of the anchor assembly. For example, the anchor can be secured to a first member, such as a member having a relatively broad surface into which or through the anchor can be disposed; a second member, such as an elongate member, can be secured by the head member to form a connection between the first and second members. Thus, the anchor assemblies can be used in a variety of situations and contexts. In one example use, an anchor assembly is used to secure a bone, such as a vertebra, to a rod, such as is done in surgical and minimally invasive spinal treatment procedures. In these procedures, a single rod can be secured to multiple anchor assemblies, effectively connecting the items connected to the anchors, such as two or more vertebrae. Connecting multiple anchor assemblies in this manner allows a user to manipulate the relative positioning of the vertebrae.

A head member, along with a compression member and retaining member, is useful for connecting to and providing additional structure for an anchor, such as a screw, nail, or barbed member.

All components of the anchor assemblies can be made from any suitable material. Non-limiting examples of suitable materials include metals, such as stainless steel, titanium, cobalt-chromium, and other metals, and plastics commonly used in medical devices. Non-limiting examples of materials considered specifically suitable for use in the compression member and retaining member include Nitinol and other superelastic materials, polyurethane materials, silicone materials, and polyether ether ketone (PEEK) materials.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

I claim:

1. An anchor assembly, comprising:
    a head member having a proximal end and a distal end, the head member defining a proximal opening at the proximal end, a distal opening at the distal end, a passageway extending from the proximal opening to the distal opening, a proximal portion having a first inner surface and defining a proximal chamber of the passageway, and a distal portion having a second inner surface defining a distal chamber of the passageway, the proximal portion defining a lateral opening continuous with the proximal opening and the second inner surface defining a channel having a proximal portion having a first depth and a distal portion having a second depth that is less than the first depth;
    a retaining member disposed within the distal portion of the channel;
    a compression member exerting a force to maintain the retaining member within the distal portion of the channel; and
    an anchor having a head and a shank, the head partially disposed within the distal chamber of the passageway;
    a sleeve partially disposed within the distal chamber of the passageway; and
    wherein the compression member is disposed between the distal end of the head member and a portion of the sleeve.

2. The anchor assembly of claim 1, wherein the compression member comprises a ring member formed of a compressible material.

3. An anchor assembly, comprising:
    a head member having a proximal end and a distal end, the head member defining a proximal opening at the proximal end, a distal opening at the distal end, a passageway extending from the proximal opening to the distal opening, a proximal portion having a first inner surface and defining a proximal chamber of the passageway, and a distal portion having a second inner surface defining a distal chamber of the passageway, the proximal portion defining a lateral opening continuous with the proximal opening and the second inner surface defining a channel having a proximal portion having a first depth and a distal portion having a second depth that is less than the first depth;
    a retaining member disposed within the distal portion of the channel;
    a compression member exerting a force to maintain the retaining member within the distal portion of the channel; and
    an anchor having a head and a shank, the head partially disposed within the distal chamber of the passageway;
    an insert disposed within the passageway;
    wherein the insert defines first and second stanchions and a notch extending between the first and second stanchions.

* * * * *